United States Patent
Kito et al.

(10) Patent No.: US 8,229,202 B2
(45) Date of Patent: Jul. 24, 2012

(54) RADIATION IMAGING APPARATUS

(75) Inventors: Eiichi Kito, Kanagawa-ken (JP); Takuya Yoshimi, Kanagawa-ken (JP); Tsuyoshi Tanabe, Kanagawa-ken (JP); Yasunori Ohta, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 880 days.

(21) Appl. No.: 12/285,085

(22) Filed: Sep. 29, 2008

(65) Prior Publication Data

US 2009/0087073 A1      Apr. 2, 2009

(30) Foreign Application Priority Data

Sep. 27, 2007   (JP) ................................. 2007-251179

(51) Int. Cl.
*G06T 1/00* (2006.01)
*H05G 1/64* (2006.01)
*H05G 1/56* (2006.01)

(52) U.S. Cl. ......... 382/132; 378/981; 378/114; 378/901

(58) Field of Classification Search .................. 382/128, 382/130–132; 378/19, 91, 98, 98.2, 98.8, 378/114–116, 210, 901

See application file for complete search history.

(56) References Cited

U.S. PATENT DOCUMENTS

| 6,205,199 | B1* | 3/2001 | Polichar et al. | 378/98.8 |
| 6,268,614 | B1 | 7/2001 | Imai | |
| 7,732,779 | B2* | 6/2010 | Kito et al. | 250/370.09 |
| 2005/0075098 | A1* | 4/2005 | Lee et al. | 455/414.1 |
| 2007/0162623 | A1* | 7/2007 | Kondo | 710/2 |
| 2007/0270115 | A1* | 11/2007 | Kravets | 455/283 |
| 2008/0009304 | A1* | 1/2008 | Fry | 455/522 |
| 2008/0049901 | A1* | 2/2008 | Tamakoshi | 378/98.2 |
| 2008/0267466 | A1* | 10/2008 | Fujita et al. | 382/128 |

FOREIGN PATENT DOCUMENTS

| JP | 7-140255 | 6/1995 |
| JP | 2003-210444 | 7/2003 |
| JP | 2006-247102 | 9/2006 |
| JP | 2006-263339 | 10/2006 |

* cited by examiner

*Primary Examiner* — Anastasia Midkiff
(74) *Attorney, Agent, or Firm* — Jean C. Edwards, Esq.; Edwards Neils PLLC (57) ABSTRACT

A radiation imaging apparatus reads out image signals from a radiation detecting section that detects radiation which has passed through a subject, and outputs the read out image signals as wireless signals. The signal strength of communications of a cassette transmitter/receiver is set to be lower during readout of the image signals than the signal strength of communications of the cassette transmitter/receiver at times other than during readout of image signals.

5 Claims, 7 Drawing Sheets

RADIATION IMAGING APPARATUS

CROSS-REFERENCE TO RELATED APPLICATIONS

The present application claims priority from Japanese Patent Application No. 2007-251179, filed Sep. 27, 2007, the contents of which are herein incorporated by reference in their entirety.

FIELD OF THE INVENTION

The present invention is related to a radiation imaging apparatus that reads out image signals from a radiation detecting section that detects radiation which has passed through a subject and outputs the image signals as wireless signals.

DESCRIPTION OF THE RELATED ART

Various radiation detectors that record radiation images of subjects when irradiated by radiation which has passed through the subjects have been proposed and are in practical use in the field of medicine and the like.

For example, there are radiation detectors that utilize semiconductors such as amorphous selenium that generate electrical charges when irradiated by radiation. Radiation detectors of this type that employ the so called optical readout method and the TFT readout method have been proposed.

Japanese Patent No. 3494683 discloses a radiation imaging system that employs the aforementioned radiation detector. In this system, radiation image signals which are detected by a radiation detector are wirelessly transmitted to a processing apparatus. Then, the processing apparatus administers signal processes, such as image processes, on the received radiation image signals.

Japanese Unexamined Patent Publication No. 2006-263339 discloses an electronic cassette that transmits radiation image signals at high frequencies, to enable large volumes of radiation image signals to be transmitted at high speeds.

Radiation image signals are output as wireless signals in the inventions disclosed in Japanese Patent No. 3494683 and Japanese Unexamined Patent Publication No. 2006-263339. If radiation image signals which have already been read out are output as wireless signals during readout of new radiation image signals from radiation image detectors, noise will occur within the radiation image signals which are currently being read out, due to influence of the radio waves of the wireless transmission, resulting in deteriorated image quality of the radiation image. This is because the radiation image signals which are read out from the radiation image detector are extremely weak signals.

Therefore, Japanese Unexamined Patent Publication No. 2006-247102 discloses a radiation imaging system in which the operation of a communications module of an imaging apparatus that outputs wireless signals is ceased during readout of radiation image signals from a radiation detector.

Japanese Unexamined Patent Publication No. 2003-210444 discloses a radiation imaging system, in which a directional antenna is used to output wireless signals such that radio waves are not irradiated onto a radiation image detector and a detecting section that reads out radiation image signals from the radiation image detector, in order to suppress the aforementioned adverse influence imparted by the wireless signals.

In the radiation imaging system disclosed by Japanese Unexamined Patent Publication No. 2006-247102, wireless communication cannot be performed while reading out radiation image signals from the radiation detector. Consequently, the processing speed of the system becomes slow. In the radiation imaging system disclosed by Japanese Unexamined Patent Publication No. 2003-210444, limitations are imposed with regard to the placement of the transmitting side (electronic cassette) and the receiving side (console) of wireless communications, which results in a system with poor operability.

SUMMARY OF THE INVENTION

The present invention has been developed in view of the foregoing circumstances. It is an object of the present invention to provide a radiation imaging apparatus, which is capable of suppressing the adverse influence imparted by wireless signals onto radiation image signals, which are being read out, without sacrificing processing speed.

A first radiation imaging apparatus of the present invention comprises:

a radiation detecting section that generates electric charges when irradiated with radiation which has passed through a subject, to record a radiation image of the subject;

a readout section that reads out image signals that represent the radiation image of the subject from the radiation detecting section; and a wireless communicating section that reads out the image signals from the readout section and outputs the read out image signals as wireless signals;

the wireless communicating section decreasing the signal strength of communications during readout of the image signals by the readout section to be lower than the signal strength of communications at times other than during readout of image signals.

In the first radiation imaging apparatus of the present invention, the wireless communicating section may set the signal strength of communications during readout of the image signals to a degree at which the wireless signals output from the wireless communicating section do not influence the image signals which are being read out.

Alternatively, the second wireless communicating section may:

set the signal strength of communications during readout of the image signals to a degree at which the wireless signals output from the wireless communicating section do not influence the image signals which are being read out;

decrease the signal strength of communications in a stepwise manner, to obtain a signal strength at a step which is greater than or equal to a minimum signal strength that enables communications between the radiation imaging apparatus and a receiving apparatus that receives the wireless signals; and set the obtained signal strength as the signal strength of communications during readout of the image signals; while:

increasing the transfer rate of the wireless signals in a stepwise manner corresponding to the stepwise decrease of the signal strength; and setting the transfer rate of the wireless signals to a speed corresponding to the obtained signal strength.

A second radiation imaging apparatus of the present invention comprises:

a radiation detecting section that generates electric charges when irradiated with radiation which has passed through a subject, to record a radiation image of the subject;

a readout section that reads out image signals that represent the radiation image of the subject from the radiation detecting section; and a wireless communicating section that reads out the image signals from the readout section and outputs the read out image signals as wireless signals;

the wireless communicating section decreasing the transfer rate of the wireless signals during readout of the image signals by the readout section to be lower than transfer rate of the wireless signals at times other than during readout of image signals.

In the second radiation imaging system of the present invention, the wireless communicating section may set the transfer rate of the wireless signals during readout of the image signals to a speed at which the wireless signals output from the wireless communicating section do not influence the image signals which are being read out.

Here, the term "during readout" refers to a period of time during which electric charges which are generated in the radiation detecting section due to irradiation by radiation are being read out as image signals.

In addition, the phrase "a degree at which the wireless signals output from the second wireless communicating section do not influence the image signals which are being read out" refers to a signal strength or a transfer rate at which no noise occurs in the image signals being read out due to the wireless signals, or to a signal strength or a transfer rate at which a negligible amount of noise occurs in the image signals.

According to the first radiation imaging apparatus of the present invention, the wireless communicating section decreases the signal strength of communications during readout of the image signals by the readout section to be lower than the signal strength of communications at times other than during readout of image signals. Therefore, the influence exerted onto the image signals, which are being read out, by the wireless signals output from the wireless communicating section can be reduced. Accordingly, the amount of noise that occurs in the image signals can also be reduced.

In the first radiation imaging apparatus of the present invention, a configuration may be adopted, wherein the second wireless communicating section: sets the signal strength of communications during readout of the image signals to a degree at which the wireless signals output from the wireless communicating section do not influence the image signals which are being read out; decreases the signal strength of communications in a stepwise manner, to obtain a signal strength at a step which is greater than or equal to a minimum signal strength that enables communications between the radiation imaging apparatus and a receiving apparatus that receives the wireless signals; and sets the obtained signal strength as the signal strength of communications during readout of the image signals; while: increasing the transfer rate of the wireless signals in a stepwise manner corresponding to the stepwise decrease of the signal strength; and setting the transfer rate of the wireless signals to a speed corresponding to the obtained signal strength. In this case, the influence exerted onto the image signals, which are being read out, by the wireless signals output from the wireless communicating section can be reduced, and the transmission time of the wireless signals can be shortened. Accordingly, the processing efficiency of the apparatus can be improved.

According to the second radiation imaging apparatus of the present invention, the wireless communicating section decreases the transfer rate of the wireless signals during readout of the image signals by the readout section to be lower than transfer rate of the wireless signals at times other than during readout of image signals. Therefore, the influence exerted onto the image signals, which are being read out, by the wireless signals output from the wireless communicating section can be reduced. Accordingly, the amount of noise that occurs in the image signals can also be reduced.

BEST MODE FOR CARRYING OUT THE INVENTION

Hereinafter, a radiation imaging system 10 that employs a radiation imaging apparatus according to a first embodiment of the present invention will be described.

Figure 1:
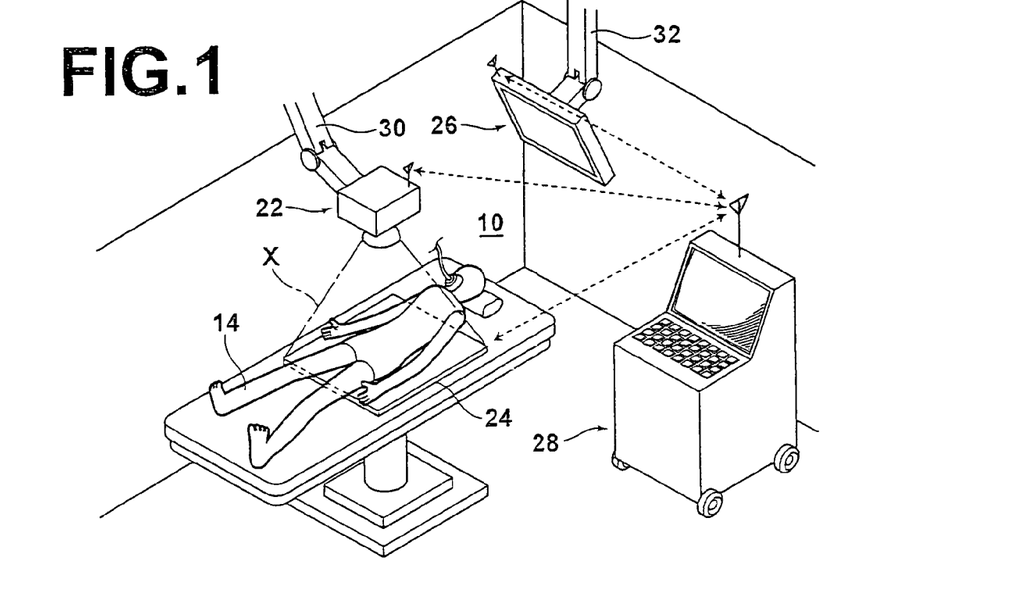
FIG. 1 is a schematic diagram that illustrates radiation imaging systems according to first through fourth embodiments of the present invention.

FIG. 1 is a diagram that illustrates an operating room in which the radiation imaging system 10 is installed.

The radiation imaging system 10 is equipped with: an imaging apparatus 22; a radiation detecting cassette 24; a display apparatus 26; and a console 28. The imaging apparatus 22 irradiates patients 14 with radiation X of a dosage according to imaging conditions. The radiation detecting cassette 24 includes a radiation detector that detects the radiation X which has passed through the patients 22 and records radiation images of the patients 22. The display apparatus 26 displays the radiation images detected by the radiation detector. The console 28 controls the operations of the imaging apparatus 22, the radiation detecting cassette 24, and the display apparatus 26. Signals are transmitted and received among the console 22, the imaging apparatus 22, the radiation detecting cassette 24 and the display apparatus 26 by wireless communications.

The imaging apparatus 22 is connected to a movable arm 30, to be movable to desired positions according to the portion of a patient 14 to be imaged, as well as to standby positions out of the way of physicians. Similarly, the display apparatus 26 is connected to a movable arm 32, to be movable to positions at which physicians can easily observe obtained radiation images.

Figure 2:
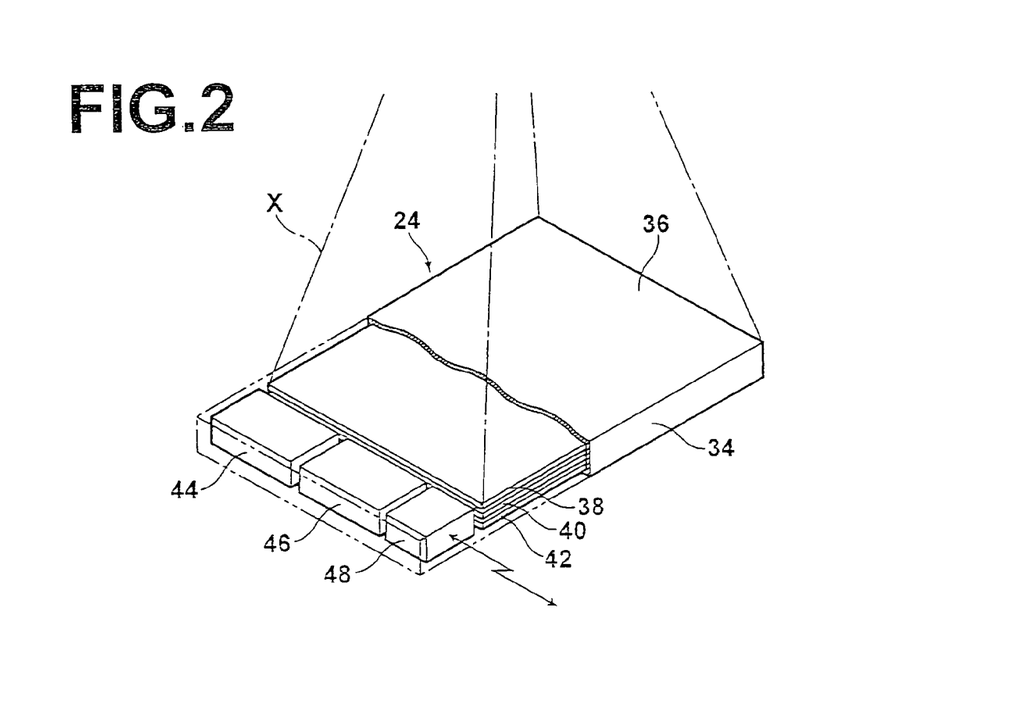
FIG. 2 is a diagram that illustrates the interior structure of a radiation detecting cassette.

FIG. 2 is a diagram that illustrates the interior structure of the radiation detecting cassette 24. The radiation detecting cassette 24 is equipped with a casing 34 which is transmissive with respect to the radiation X. A grid 38, for removing rays of the radiation X scattered by the patient 14; a radiation detector 40, for detecting the radiation X which has passed through the patient 14 and for recording a radiation image of the patient 14; and a lead plate 42, for absorbing backscattered radiation X, are provided within the casing 34 in this order from the surface 36 of the casing 34 onto which the radiation X is irradiated. Note that the surface 36 of the casing 34 onto which the radiation X is irradiated may be configured to be the grid 38.

Figure 4:
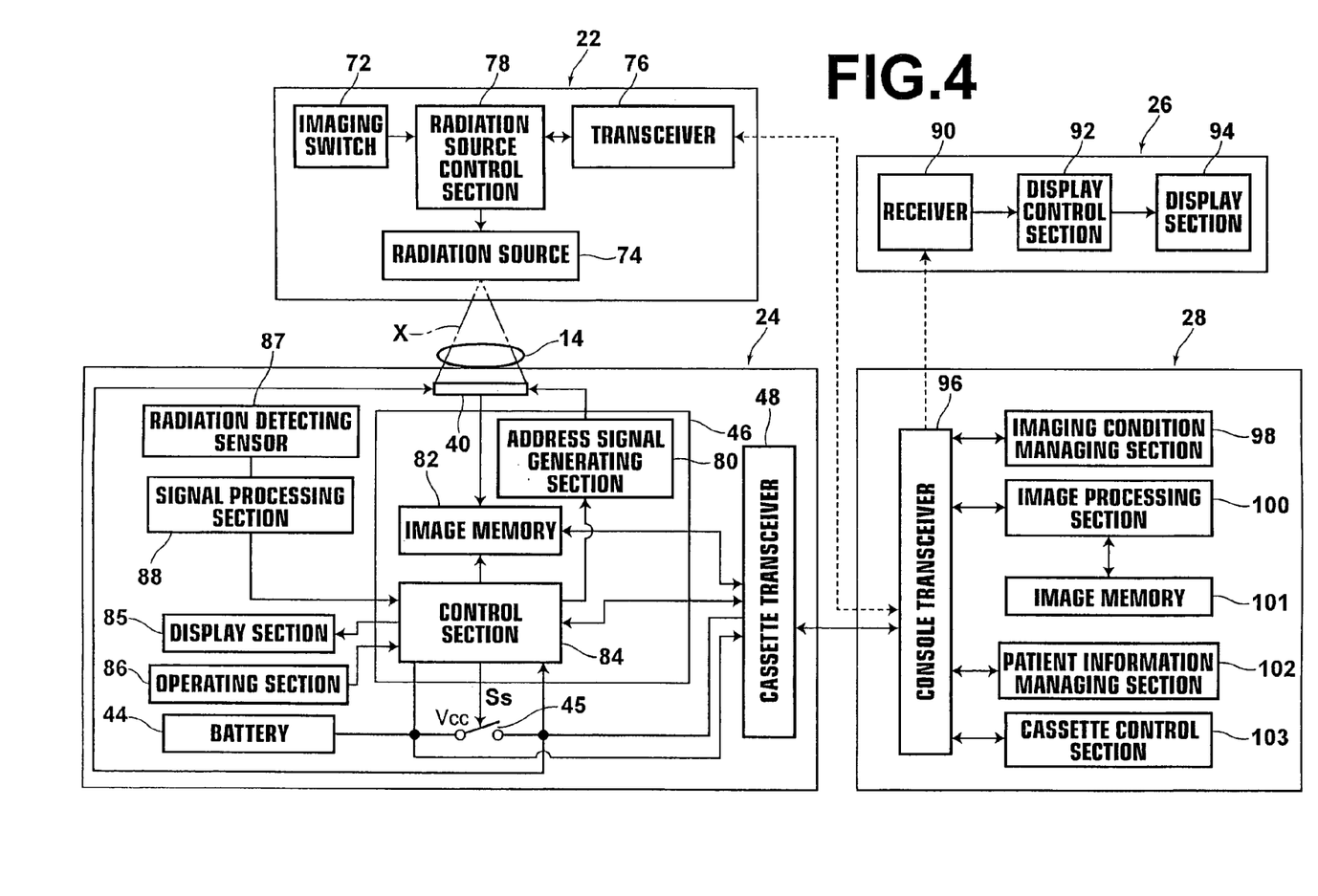
FIG. 4 is a schematic block diagram of the radiation imaging system.

A battery 44, which is the power source of the radiation detecting cassette 24; a cassette control section 46, for driving and controlling the radiation detector 40 by power supplied from the battery 44; and a cassette transceiver 48, for transmitting radiation image signals read out from the radiation detector 40 and the like to the console 28 as wireless signals, and for receiving control signals and the like from the console 28, are also housed within the casing 34. Note that it is preferable for lead plates to be provided on the cassette control section 46 and the cassette transceiver 48 toward the sides thereof that face the surface 36 of the casing 34 onto which the radiation X is irradiated, in order to avoid damage due to irradiation by the radiation X. Although omitted from FIG. 2, a display section 85 and an operating section 86 are also provided on the radiation detecting cassette 24, as illustrated in FIG. 4. The display section 85 displays radiation images detected by the radiation detector 40 and the like. The operating section 86 is provided to enable input of operating signals to the radiation detecting cassette 24. Further, a radiation detecting sensor 87, for detecting the irradiated radiation X; and a signal processing section 88, for administering predetermined signal processes on the signals detected by the radiation detecting sensor 87 are provided. A control section 84 generates control signals for automatic exposure based on the signal detected by the radiation detecting sensor 87, and transmits the control signals to the console 28 via the cassette transceiver 48.

Figure 3:
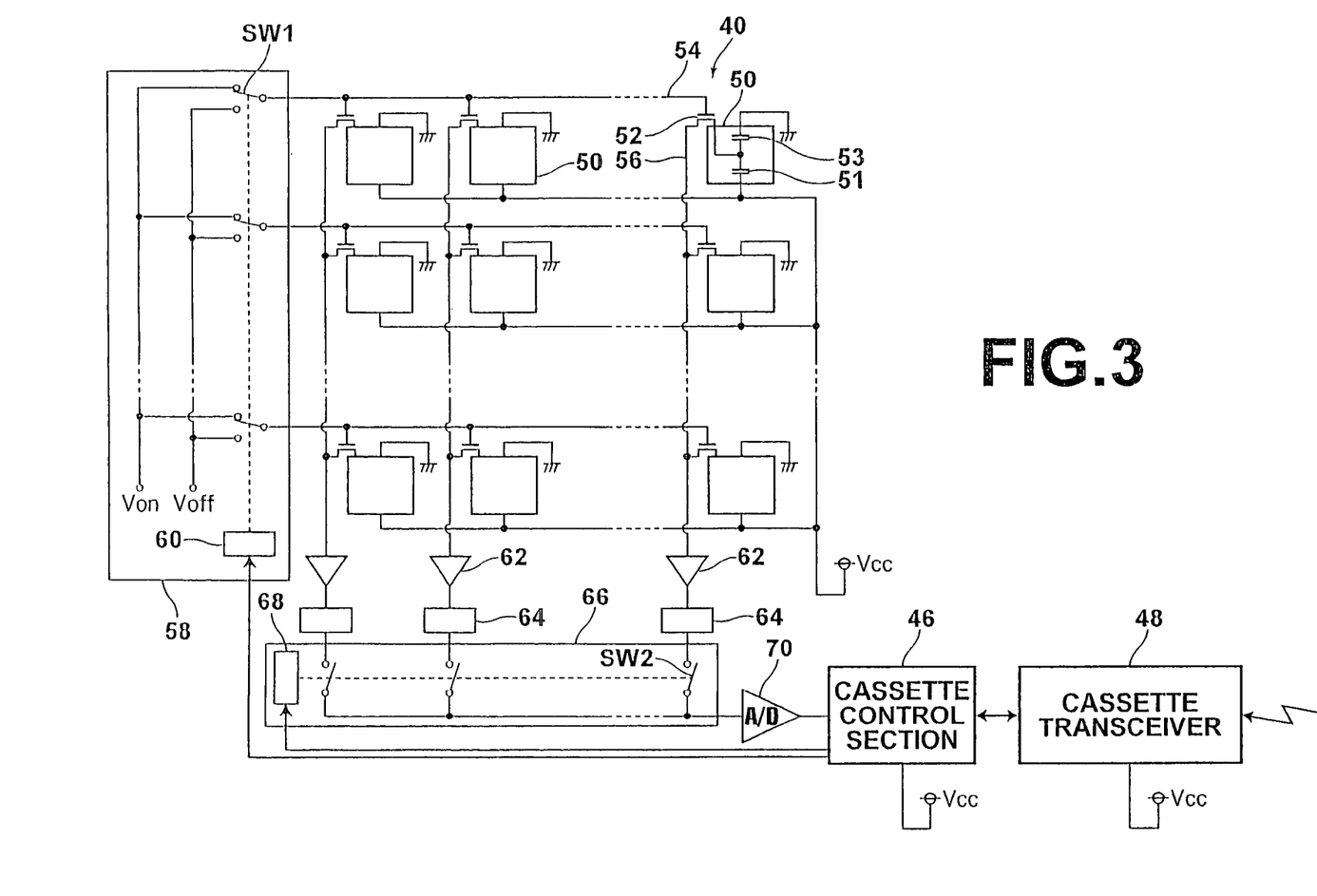
FIG. 3 is a block diagram that illustrates the circuit structure of a radiation detector.

FIG. 3 is a block diagram that illustrates the circuit structure of the radiation detector 40. The radiation detector 40 is of a structure in which a photoelectric converting layer 51 formed by a substance that senses the radiation X and generates electric charges, such as amorphous selenium (a-Se) is provided on a TFT (Thin Film Transistor) array, in which TFT's 52 are provided in an array. The electric charges which are generated in the photoelectric converting layer 51 are accumulated in a charge accumulating capacitor 53. Then, each row of TFT's 52 are sequentially turned ON, to read out the electric charges accumulated in the charge accumulating capacitor 53 as image signals. In FIG. 3, the connective relationship between a single pixel 50 and a single TFT 52 is shown, and the structures that constitute other pixels 50 are omitted. Note that the structure of amorphous selenium changes at high temperatures, and the function thereof deteriorates. Therefore, it is necessary to use the photoelectric converting layer 51 within a predetermined temperature range. Accordingly, it is preferable for a cooling means for cooling the radiation detector 40 to be provided within the radiation detecting cassette 24.

A gate line 54 that extends parallel to the row direction of the TFT's 52 and a signal line 56 that extends parallel to the column direction of the TFT's 52 is connected to each TFT 52 which is connected to each pixel 50 of the radiation detector 40. Each gate line 54 is connected to a line scanning drive section 58, and each signal line 56 is connected to a multiplexer 66.

Control signals Von and Voff, for controlling the TFT's 52 arranged in the row direction to be turned ON and OFF, are supplied to the gate lines 54 from the line scanning drive section 58. In this case, the line scanning drive section 58 is equipped with a plurality of switches SW1, for switching among the gate lines 54, and an address decoder 60 for outputting a selection signal that selects one of the switches SW1. Address signals are supplied to the address decoder 60 from the cassette control section 46.

Electric charges which are held in the charge accumulating capacitors 53 for each pixel 50 flow to the signal lines 56, via the TFT's 52, which are arranged in the column direction. These electric charges are amplified by amplifiers 62. The multiplexer 66 is connected to the amplifiers 62 via sample holding circuits 64. The multiplexer 66 is equipped with a plurality of switches SW2, for switching among the signal lines 56, and an address decoder 68 for outputting a selection signal that selects one of the switches SW2. Address signals are supplied to the address decoder 68 from the cassette control section 46. An A/D converter 70 is connected to the multiplexer 66, and radiation image signals, which are converted to digital signals by the A/D converter, are output to the cassette control section 46.

FIG. 4 is a schematic block diagram of the radiation imaging system 10, constituted by the imaging apparatus 22, the radiation detecting cassette 24, the display apparatus 26 and the console 28.

The imaging apparatus 22 is equipped with: an imaging switch 72; a radiation source 74 that outputs the radiation X; a transceiver 76 that receives imaging conditions from the console 28 by wireless communications, and transmits imaging completion signals and the like to the console 28 by wireless communications; and a radiation source control section 78 that controls the radiation source 74, based on imaging start signals supplied by the imaging switch 72 and imaging conditions supplied by the transceiver 76. Note that in cases that automatic exposure control is performed based on signals detected by the radiation detecting sensor 87 of the radiation detecting cassette 24, the control signal generated based on the signals detected by the radiation detecting sensor 87 is output from the cassette control section 46 to the console 28 via the cassette transceiver 48. Then, the console 28 outputs a control signal to the imaging apparatus 22. The control signal is input to the radiation source control section 78 via the transceiver 76. Finally, the radiation source control section 78 ceases emission of radiation from the radiation source 74.

The radiation detector 40, the battery 44, the cassette control section 46, the cassette transceiver 48, and a power switch 45 are housed in the radiation detecting cassette 24. The power switch 45 is turned ON and OFF by control signals Ss output from the control section 84, to switch the supply of power from the battery 44 to the radiation detector 40, the cassette control section 46, and the cassette transceiver 48 ON and OFF. The control section 84 outputs the control signals Ss to the power switch 45, based on control signals input thereto from the console 28 via the cassette transceiver 48.

The cassette control section 46 is equipped with: an address signal generating section 80 that supplies the address decoder 60 of the line scanning drive section 58 of the radiation detector 40 and the address decoder 68 of the multiplexer 66 with address signals; an image memory 82 for storing the radiation image signals which are read out from the radiation detector 40; and the control section 84 that controls the operations of the address signal generating section 80, the image memory 82, and the cassette transceiver 48. The control section 84 outputs signals indicating that radiation image signals are being read out from the radiation detector 40 to the cassette transceiver 48, as will be described later. The signals output from the control section 84 are not limited to those that indicate that radiation image signals are being read out form the radiation detector 40. Various types of information regarding the radiation detecting cassette 24, such as the operating state of the radiation detector 40, are output to the console 28 via the cassette transceiver 48. For example, a temperature sensor may be provided in the radiation detecting cassette 24, and information regarding the temperature may be output to the console 28 via the cassette transceiver 48. In addition, the control section 84 receives various control signals issued to the radiation detecting cassette 24 from the console 28 via the cassette transceiver 48, in addition to the control signals Ss for turning the power switch 45 ON and OFF.

The display apparatus 26 is equipped with: a receiver 90 that receives radiation image signals from the console 28; a display control section 92 that controls the display of the received radiation image signals; and a display section 94 that displays radiation images based on the radiation image signals which have been processed by the display control section 92.

The console 28 is equipped with a console transceiver 96 that transmits and receives necessary information, including radiation image signals, to and from the imaging apparatus 22, the radiation detecting cassette 24, and the display apparatus 26 as wireless signals; an imaging condition managing section 98 that manages imaging conditions which are necessary for the imaging apparatus 22 to perform imaging operations; an image processing section 100 that administers image processes on radiation image signals transmitted from the radiation detecting cassette 24; an image memory 101 that records radiation image signals on which image processes have been administered; a patient information managing section 102 that manages information regarding patients 14 who are the subjects of imaging; and a cassette control section 103 that outputs various control signals to the radiation detecting cassette 24, such as the control signals for turning the power switch 45 ON, and receives various types of information regarding the radiation detecting cassette 24, such as the operating state of the radiation detecting cassette 24.

Note that the term "imaging conditions" refers to conditions that determine X-ray tube voltage, X-ray tube current, irradiation time, and the like, such that the radiation X is irradiated at appropriate dosages onto imaged portions of the patients. For example, the "imaging conditions" may be conditions such as "portion to be imaged" and "imaging method". The term "patient information" refers to information that specifies each patient 14, such as the name, the sex, and the patient ID number of the patients 14. Imaging ordering information that includes the imaging conditions and the patient information can be set at the console 28.

Figure 5:
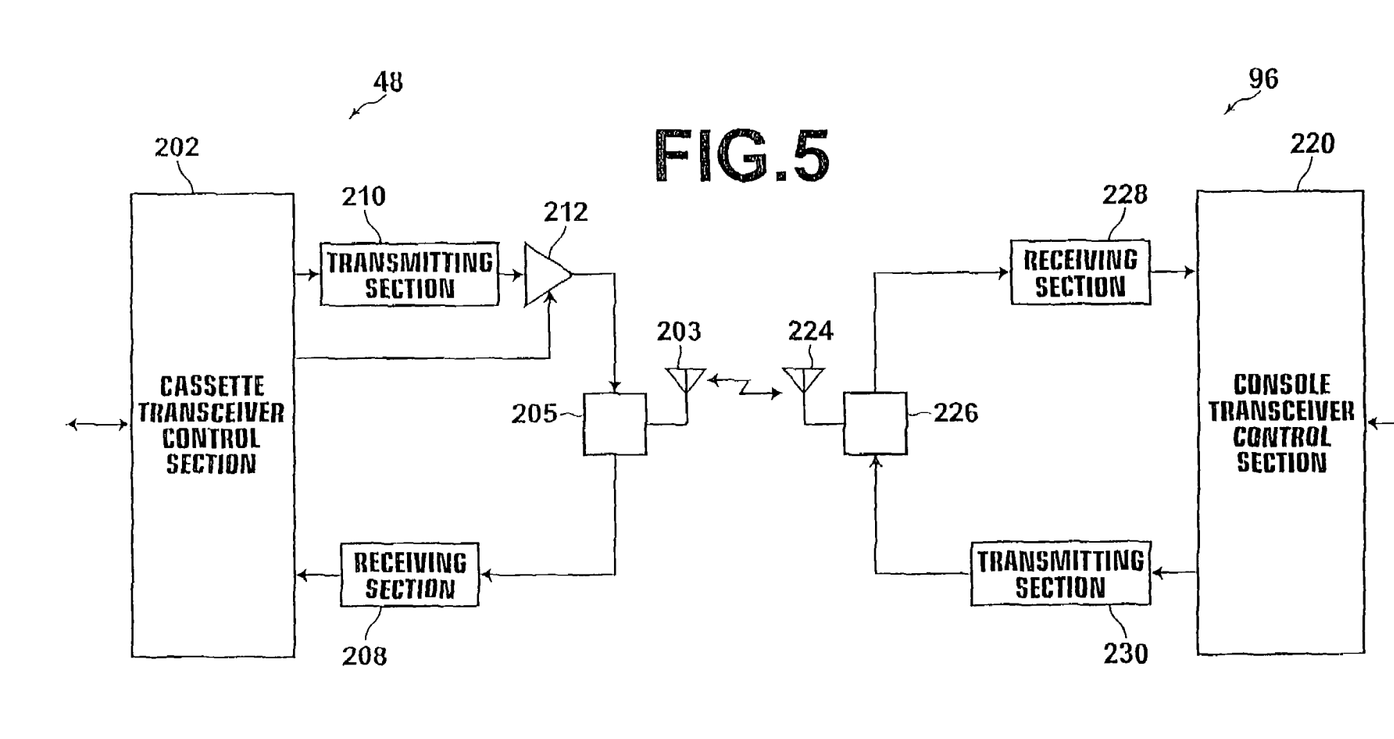
FIG. 5 is a block diagram that illustrates a portion of the inner structures of a cassette transceiver of a radiation detecting cassette and a console transceiver of a console.

FIG. 5 is a block diagram that illustrates the inner structures of the cassette transceiver 48 of the radiation detecting cassette 24 and the console transceiver 96 of the console 28.

The cassette transceiver 48 of the radiation detecting cassette 24 is equipped with: a cassette transceiver control section 202 including a microcomputer; an antenna 203; an antenna duplexer 205; a receiving section 208; a transmitting section 210; and a variable gain amplifier 212.

The receiving section 208 demodulates radio waves which are received by the antenna 203 and input to the receiving section 208 via the antenna duplexer 205. The demodulated radio waves are output to the cassette transceiver control section 202 as received signals. The transmitting section 210 modulates and outputs radiation image signals, which are read out from the image memory 82 (refer to FIG. 4) and output from the cassette transceiver control section 202 at a predetermined transfer rate.

The variable gain amplifier 212 amplifies the signals output from the transmitting section 210 at a set gain, and outputs transmission signals. The gain level of the variable gain amplifier 212 is switched according to control signals output from the cassette transceiver control section 202. The cassette transceiver control section 202 sets the gain to be lower during readout of the image signals from the radiation detector 40, as indicated by signals from the control section 84 (refer to FIG. 4), than the gain at times other than during readout of image signals. Thereby, the signal strength of communications of the cassette transceiver 48 is set to be lower during readout of radiation image signals than during times other than during readout of radiation image signals. Note that the gain level of the variable gain amplifier 212 during readout of the radiation image signals from the radiation detector 40 is set to a value at which the wireless signals output from the cassette transceiver 48 do not influence the radiation image signals which are being read out. This gain level may be obtained in advance, and set at the cassette transceiver control section 202. Alternatively, noise levels may be detected from radiation image signals which are being read out while wireless signals are being output, and the gain level may be set to that at which the noise level is lower than a predetermined threshold value.

Meanwhile, the console transceiver 96 is equipped with: a console transceiver control section 220 including a microcomputer; an antenna 224; an antenna duplexer 226; a receiving section 228; and a transmitting section 230.

The receiving section 228 demodulates radio waves which are received by the antenna 224 and input to the receiving section 228 via the antenna duplexer 226. The demodulated radio waves are output to the console transceiver control section 96 as received signals. The transmitting section 230 modulates and outputs radiation image signals, which are output from the console transceiver control section 96.

Next, the operation of the radiation imaging system 10 that employs the first embodiment will be described.

The radiation imaging system 10 is installed in an operating room 12, and used by a physician when radiation imaging of a patient becomes necessary during surgery, for example. For this reason, the patient information of the patient 14 who is the subject of imaging is registered in the patient information managing section 102 of the console 28 in advance, prior to imaging operations being performed. In addition, in the case that portions to be imaged and imaging methods are also set in advance, these imaging conditions are registered in the imaging condition managing section 98 in advance. Surgery on the patient 14 is initiated in a state in which the preparatory steps described above have been completed.

In the case that radiation imaging is to be performed during surgery, the physician or a radiological technician sets the radiation detecting cassette 24 at a predetermined position between the patient 14 and an operating table 16 such that the surface 36 onto which radiation is irradiated faces the imaging apparatus 22.

Next, the physician or the radiological technician operates the console 28 to output a control signal from the cassette control section 103 to turn the power switch 45 of the radiation detecting cassette 24 ON. The control signal is output from the console 28 via the console transceiver 96. The control signal is received by the cassette transceiver 48 of the radiation detecting cassette 24, and output to the control section 84. The control section 84 outputs a control signal to the power switch 45 to turn the power switch 45 ON. When the power switch 45 of the radiation detecting cassette 24 is turned ON, various types of information, such as the operating state of the radiation detecting cassette 24, are output from the control section 84 of the cassette control section 46. The information is output to the console 28 via the cassette transceiver 48.

Here, the signals that represent the various types of information regarding the radiation detecting cassette 24 are output from the cassette transceiver control section 202 of the cassette transceiver 48 to the transmitting section 210 at a predetermined transfer rate. The signals are modulated at the transmitting section 210, amplified by the variable gain amplifier 212, then output to the console 28 via the antenna duplexer 205 and the antenna 203. At this time, the cassette transceiver control section 202 is not receiving a signal from the control section 84 that indicates that radiation image signals are being read out from the radiation detector 40. Therefore, the gain level of the variable gain amplifier 212 is set at a level which is higher than that which is set during readout of radiation image signals, that is, a gain level which is used during standard wireless communications. As described above, the cassette transceiver control section 202 sets the gain level of the variable gain amplifier 212 at a higher level than the gain set during readout of radiation image signals, while signals indicating that radiation image signals are being read out are not being received from the control section 84.

Next, the imaging apparatus 22 is moved to a position that faces the radiation detecting cassette 24 and the imaging switch 72 is operated to perform an imaging operation.

The radiation source control section 78 of the imaging apparatus 22 obtains imaging conditions for the portion of the patient 14 to be imaged from the image condition managing section 98 of the console 28, via the console transceiver 96 and the transceiver 76. The radiation source 74 is controlled according to the obtained imaging conditions, to irradiate radiation X of a predetermined dosage onto the patient 14.

The radiation X which has passed through the patient 14 is irradiated onto the radiation detector 40 after scattered rays are removed by the grid 38 of the radiation detecting cassette 24. The photoelectric converting layer 51 that constitutes the radiation detector 40 converts the radiation X into electric signals, and the charge accumulating capacitors 53 corresponding to each pixel 50 holds the electric signals as electric charges (refer to FIG. 3).

Here, the radiation X which is irradiated toward the radiation detecting cassette 24 is detected by the radiation detecting sensor 87 provided in the radiation detecting cassette 24 as well as by the radiation detector 40. In the case that automatic exposure control is performed based on signals detected by the radiation detecting sensor 87 of the radiation detecting cassette 24, an automatic exposure control signal generated based on the signals detected by the radiation detecting sensor 87 is output from the control section 84 of the cassette control section 46 to the console 28 via the cassette transceiver 48. At this time as well, the cassette transceiver control section 202 is not receiving a signal from the control section 84 that indicates that radiation image signals are being read out from the radiation detector 40. Therefore, the gain level of the variable gain amplifier 212 is set at a level which is higher than that which is set during readout of radiation image signals, that is, a gain level which is used during standard wireless communications.

A control signal is output from the console 28 to the imaging apparatus 22 in response to the automatic exposure control signal transmitted to the console 28 from the radiation detecting cassette 24. The control signal is input to the radiation source control section 78 via the transceiver 76. The radiation source control section 78 ceases emission of radiation from the radiation source 74, based on the control signal.

After irradiation of the radiation X is ceased as described above, the electric charges which are held in each of the charge accumulating capacitors 53 of the radiation detector 40 are read but according to address signals which are output from the address signal generating section 80 of the cassette control section 46 to the line scanning drive section 58 and the multiplexer 66.

That is, the address decoder 60 of the line scanning drive section 58 outputs a selection signal according to an address signal supplied thereto the address signal generating section 80, to select one of the switches SW1. When the switch SW1 is selected, the control signal Von is supplied to the gate of the TFT 52 connected to the gate line corresponding to the switch SW1. Meanwhile, the address decoder 68 of the multiplexer 66 outputs selection signals according to the address signals supplied thereto by the address signal generating section 80 to sequentially select the switches SW2. Thereby, the electric charge signals which are held in the charge accumulating capacitors 53 corresponding to each pixel 50 connected to the gate line 54 which has been selected by the line scanning drive section 58 are sequentially read out via the signal lines 56.

The electric charge signals, which have been read out from the charge accumulating capacitors 53 corresponding to each pixel 50 connected to the selected gate line 54 of the radiation detector, are amplified by the amplifiers 62 connected to each of the signal lines 56. The amplified signals are sampled by each of the sample holding circuits 64 connected to the amplifiers 62, then supplied to the A/D converter 70 via the multiplexer 66, where they are converted to digital signals. The radiation image signals which have been converted to digital signals are temporarily recorded in the image memory 82 of the cassette control section 46.

The address decoder 60 of the line scanning drive section 58 sequentially switches the switch SW1 which is selected according to the address signals supplied thereto by the address signal generating section 80. Thereby, the electric charge signals, which are held in the charge accumulating capacitors 53 corresponding to each pixel 50 connected to the gate line 54 selected by the line scanning drive section 58, are sequentially read out via the signal lines 56. The signals are recorded in the image memory 82 of the cassette control section 46 via the multiplexer 66 and the A/D converter 70.

The control section 84 of the cassette control section 46 sequentially reads out units of radiation image signals necessary for transmission from the image memory 82 prior to radiation image signals corresponding to a single frame being recorded in the image memory 82. The read out units of radiation image signals are output to the cassette transceiver 48.

The cassette transceiver control section 202 outputs the units of radiation image signals to the transmitting section 210 at a predetermined transfer rate. Then, the radiation image signals are modulated by the transmitting section 210, amplified by the variable gain amplifier 212, then transmitted to the console 28 as wireless signals via the antenna duplexer 205 and the antenna 203.

Here, when radiation image signals are being read out from the radiation image detector 40 as described above, a signal indicating that radiation image signals are being read out is output from the control section 84 of the cassette control section 46. This signal is input to the cassette transceiver control section 202 of the cassette transceiver 48. The cassette transceiver control section 202 outputs a control signal to the variable gain amplifier 212 according to the signal, and lowers the gain level of the variable gain amplifier 212 to a preset gain level. Note that the preset gain level of the variable gain amplifier 212 which is set during readout of the radiation image signals from the radiation detector 40 is that at which the wireless signals output from the cassette transceiver 48 do not influence the radiation image signals which are being read out, as described previously.

After readout of the radiation image signals from the radiation detector 40 is completed, the signal that indicates that readout is being performed is no longer output from the control section 84 of the cassette control section 46. At this time, the cassette transceiver control section 202 outputs a control signal to the variable gain amplifier 212 to increase the gain level to that which is used during standard wireless communications.

After readout of the radiation image signals from the radiation detector 40 is completed, the radiation image signals which are still recorded in the image memory 82 are amplified at the standard communication gain level, and output from the cassette transceiver 48.

The modulated signals transmitted to the console 28 are demodulated by the console transceiver 96 as radiation image signals. Predetermined image processes are administered to the demodulated radiation image signals by the image processing section 100, then the processed image signals are correlated with the patient information registered in the patient information managing section 102, and recorded in the image memory 101.

Thereafter, the radiation image signals, which have undergone the image processes, are transmitted from the console transceiver 96 to the display apparatus 26. The display apparatus 26, which has received the radiation image signals through the receiver 90, controls the display section 94 with the display control section 92, and displays a radiation image on the display section 94.

In the radiation imaging system that employs the radiation imaging apparatus according to the first embodiment of the present invention, the cassette transceiver 48 decreases the signal strength of communications during readout of the radiation image signals to be lower than the signal strength of communications at times other than during readout of the radiation image signals. Therefore, the influence exerted onto the radiation image signals, which are being read out, by the wireless signals output from the cassette transceiver 48 can be reduced. Accordingly, the amount of noise that occurs in the radiation image signals can also be reduced.

Next, a radiation imaging system that employs a radiation imaging apparatus according to a second embodiment of the present invention will be described.

The radiation imaging system that employs the second embodiment is of substantially the same configuration as the radiation imaging system of that employs the first embodiment described above. However, the radiation imaging system that employs the second embodiment differs from the first embodiment in the method by which the signal strength of the cassette transceiver 48, that is, the gain level of the variable gain amplifier 212, and the transfer rate of the signals output from the cassette transceiver control section 202 during readout of radiation image signals, are determined.

In the radiation imaging system that employs the second embodiment, the signal strength of the cassette transceiver 48, that is, the gain level of the variable gain amplifier 212, and the transfer rate of the signals output from the cassette transceiver control section 202 during readout of radiation image signals, are determined after the power switch 45 of the radiation detection cassette 24 is turned ON. The gain level and the transfer rate are determined prior to imaging operations of radiation images are initiated.

First, a test signal is generated by the control section 84 of the cassette control section 46. The test signal is output to the cassette transceiver control section 202 of the cassette transceiver 48. Next, the cassette transceiver control section 202 outputs the input test signal to the transmitting section 210 at a predetermined transfer rate. The test signal is modulated by the transmitting section 210, amplified by the variable gain amplifier 212, then transmitted to the console 28 as a wireless signal via the antenna duplexer 205 and the antenna 203.

At this time, the gain level of the variable gain amplifier 212 is set to a value (hereinafter, referred to as "first gain level") at which the wireless signals output from the cassette transceiver 48 do not influence radiation image signals which are being read out. The first gain level is set in the cassette transceiver control section 202 in advance. The transfer rate when the test signal is output to the transmitting section 210 is the slowest possible transfer rate (hereinafter, referred to as "first transfer rate"). The first transfer rate is also set in advance.

The console 28 receives the test signal output from the radiation detecting cassette 24 in the manner described above with the console transceiver 96. The received test signal is input to the cassette control section 103.

The cassette control section 103 judges whether the signal strength of the input test signal is higher than a minimum signal strength (hereinafter, referred to as "minimum communicable condition") which is capable of being transmitted between the radiation detecting cassette 24 and the console 28. Note that the minimum communicable condition is set in advance by the cassette control section 103.

In the case that the signal strength of the input test signal is higher than the minimum communicable condition, the cassette control section 103 outputs a signal (hereinafter, referred to as "communication possible signal") indicating this fact to the radiation detecting cassette 24 via the console transceiver 96.

The radiation detecting cassette 24 receives the communication possible signal via the cassette transceiver 48, and the communication possible signal is input to the cassette transceiver control section 202. When the communication possible signal is input, the cassette transceiver control section 202 sets the gain level of the variable gain amplifier 212 to a second gain level which is lower than the first gain level. At the same time, the cassette transceiver control section 202 sets the transfer rate to the transmitting section 210 to a second transfer rate, which is higher than the first transfer rate.

Then, the test signal is output again from the control section 84, output to the transmitting section 210 at the second transfer rate from the cassette transceiver control section 202, amplified at the second gain level by the variable gain amplifier 212, and transmitted to the console 28 via the antenna duplexer 205 and the antenna 203.

The console 28 receives the test signal output from the radiation detecting cassette 24 with the console transceiver 96 as described above. The received test signal is input to the cassette control section 103.

The cassette control section 103 judges whether the signal strength of the input test signal is higher than the minimum communicable condition again.

In the case that the signal strength of the input test signal is higher than the minimum communicable condition, the cassette control section 103 outputs a communication possible signal to the radiation detecting cassette 24 via the console transceiver 96 again.

The radiation detecting cassette 24 receives the communication possible signal via the cassette transceiver 48, and the communication possible signal is input to the cassette transceiver control section 202. When the communication possible signal is input, the cassette transceiver control section 202 sets the gain level of the variable gain amplifier 212 to a third gain level which is lower than the second gain level. At the same time, the cassette transceiver control section 202 sets the transfer rate to the transmitting section 210 to a third transfer rate, which is higher than the second transfer rate.

Then, the test signal is output again from the control section 84, output to the transmitting section 210 at the third transfer rate from the cassette transceiver control section 202, amplified at the third gain level by the variable gain amplifier 212, and transmitted to the console 28 via the antenna duplexer 205 and the antenna 203.

The console 28 receives the test signal output from the radiation detecting cassette 24 with the console transceiver 96 as described above. The received test signal is input to the cassette control section 103.

The cassette control section 103 judges whether the signal strength of the input test signal is higher than the minimum communicable condition again.

In the case that the signal strength of the test signal is lower than the minimum communicable condition, the cassette control section 103 outputs a signal (hereinafter, referred to as "communication impossible signal") indicating this fact to the radiation detecting cassette 24 via the console transceiver 96.

The radiation detecting cassette 24 receives the communication impossible signal via the cassette transceiver 48, and the communication impossible signal is input to the cassette transceiver control section 202. When the communication impossible signal is received, the cassette transceiver control section 202 obtains the second gain level, which is greater than the third gain level and satisfies the minimum communicable condition. At the same time, the cassette transceiver control section 202 obtains the second transfer rate, which is lower than the third transfer rate. The second gain level and the second transfer rate are set as the gain level and the transfer rate to be employed for communications during readout of radiation images.

As described above, the gain level of the variable gain amplifier 212 is decreased in a stepwise manner, and the transfer rate is increased corresponding to the stepwise decreases in gain level. When the communication impossible signal is output from the console 28, the gain level and the transfer rate of the immediately preceding step in the stepwise decrease and increase are set as the gain level and the transfer rate to be employed for communications during readout of radiation images.

Figure 6:
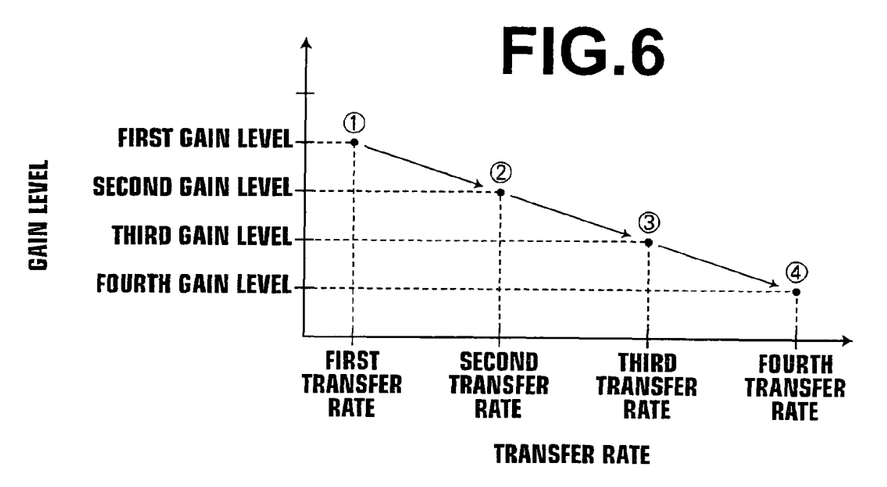
FIG. 6 is a graph for explaining a method for setting gain levels and transfer rates during readout in the radiation imaging system of the second embodiment.

Note that the transfer rates corresponding to the first through fourth gain levels illustrated in FIG. 6 are set in advance. The transfer rates are set such that they do not adversely influence radiation image signals which are being read out, when radiation image signals are amplified at the gain level for each step and output from the radiation detecting cassette 24 as wireless signals.

In the radiation imaging system of that employs the second embodiment of the present invention, during readout of radiation image signals from the radiation detector 40, that is, while the signal that indicates that readout is being performed is being output from the control section 84 of the cassette control section 46 to the cassette transceiver control section 202, the gain level of the variable gain amplifier 212 and the transfer rate of the cassette transceiver control section 202 are set in the manner described above. When the signal indicating that readout is being performed ceases to be output from the control section 84 of the cassette control section 46, the gain level of the variable gain amplifier 212 and the transfer rate of the cassette transceiver control section 202 are set to a gain level and a transfer rate which is used during standard wireless communications.

According to the radiation imaging system that employs the second embodiment, the signal strength of wireless communications during readout of the radiation image signals is decreased to a level which is close to the minimum signal strength that enables communications between the radiation detecting cassette 24 and the console 28. At the same time, the transfer is increased corresponding to the decrease of the signal strength. Therefore, the influence exerted onto the image signals, which are being read out, by the wireless signals output from the cassette transceiver 48 can be reduced. Accordingly, the occurrence of noise in the radiation image signals can be decreased. In addition, the transmission time of the radiation image signals can be shortened. Accordingly, the processing efficiency of the apparatus can be improved.

Next, a radiation imaging system that employs a radiation imaging apparatus according to a third embodiment of the present invention will be described.

The radiation imaging system that employs the third embodiment is of substantially the same configuration as the radiation imaging system that employs the first embodiment described above. However, the radiation imaging system that employs the third embodiment differs from that which employs the first embodiment in that the signal strength of the cassette transceiver 48, that is, the gain level of the variable gain amplifier 212, is not decreased during readout of radiation image signals from the radiation detector 40. Instead, the gain level of the variable gain amplifier 212 is kept constant, and the transfer rate of the signals output from the cassette transceiver control section 202 of the cassette transceiver is varied.

Specifically, a signal indicating that radiation image signals are being read out from the radiation detector 40 is output from the control section 84 of the cassette control section 46. This signal is input to the cassette transceiver control section 202 of the cassette transceiver 48. In response to this signal, the cassette transceiver control section 202 decreases the transfer rate at which radiation image signals are transferred to the transmitting section 210 to a preset speed. Note that the transfer rate during readout of radiation image signals from the radiation detector 40 is set such that wireless signals output from the cassette transceiver 48 do not adversely influence the radiation image signals which are being read out.

After readout of the radiation image signals from the radiation detector 40 is completed, the signal that indicates that readout is being performed is no longer output from the control section 84 of the cassette control section 46. At this time, the cassette transceiver control section 202 increases the transfer rate at which radiation image signals are transferred to the transmitting section 210 to a transfer rate which is used during standard wireless communications.

After readout of the radiation image signals from the radiation detector 40 is completed, the radiation image signals which are still recorded in the image memory 82 are output from the cassette transceiver control section 202 to the transmitting section 210 at the standard communication transfer rate.

As described in the first embodiment, various types of information regarding the radiation detecting cassette 24 may be output to the console 28. At this time, the cassette transceiver 202 is not receiving the signal from the control section 84 that indicates that radiation image signals are being read out from the radiation detector 40. Therefore, the transfer rate at which radiation image signals are transferred to the transmitting section 210 is set at the standard communication transfer rate, which is higher than the transfer rate which is set during readout of radiation images.

Automatic exposure control may be performed, by an automatic exposure control signal generated based on signals detected by the radiation detecting sensor 87 being output from the radiation detecting cassette 24 to the console 28. At this time as well, the cassette-transceiver-control section 202 is not receiving a signal from the control section 84 that indicates that radiation image signals are being read out from the radiation detector 40. Therefore, the transfer rate at which radiation image signals are transferred to the transmitting section 210 is set to be higher than that which is set during readout of radiation image signals, that is, a transfer rate which is used during standard wireless communications.

According to the radiation imaging system that employs the third embodiment, the transfer rate of the cassette transceiver control section 202 is set to be lower during readout of radiation image signals from the radiation detector 40 than the transfer rate at times other than during readout of the radiation signals. Therefore, the influence exerted onto the image signals, which are being read out, by the wireless signals output from the cassette transceiver 48 can be reduced. Accordingly, the amount of noise that occurs in the image signals can also be reduced.

Next, a radiation imaging system that employs a radiation imaging apparatus according to a fourth embodiment of the present invention will be described.

The radiation imaging systems that employ the first through third embodiments described above vary the signal strength and the transfer rate of wireless communications from the radiation detecting cassette 24, taking the adverse influence imparted onto the radiation image signals, which are being read out from the radiation detector 40, by the wireless signals output from the radiation detecting cassette 24 into consideration. The radiation imaging system that employs the fourth embodiment further takes adverse influence imparted onto the radiation image signals, which are being read out from the radiation detector 40, by wireless signals output from the console 28 into consideration. That is, the radiation imaging system that employs the fourth embodiment takes the signal strength of wireless communications from the console 28 into consideration. Note that control signals that may be output from the console 28 to the radiation detecting cassette 24 during readout of radiation image signals from the radiation detector 40 include reception error signals. Specifically, radiation image signals are transmitted from the radiation detecting cassette 24 to the console 28 in predetermined block units. The console 28 receives the radiation image signals in the block units, and judges whether the radiation image signals for each block have been correctly received by performing parity checks and the like. If a reception error is detected for radiation image signals in a certain block, a control signal that prompts the radiation detecting cassette 24 to resend the radiation image signals of the block, for which the error has been detected, is output. In the above description, control signals are output from the console 28 to the radiation detecting cassette 24 only in cases that reception errors are detected. Alternatively, a signal that indicates that reception was completed or a signal that indicates that a reception error has been detected may be output from the console 28 to the radiation detecting cassette 24, for each block.

The radiation imaging system that employs the fourth embodiment is of substantially the same configuration as the radiation imaging systems that employ the first through third embodiments described above. Therefore, a description will be given mainly regarding structures which are different from those of the first through third embodiments.

Figure 7:
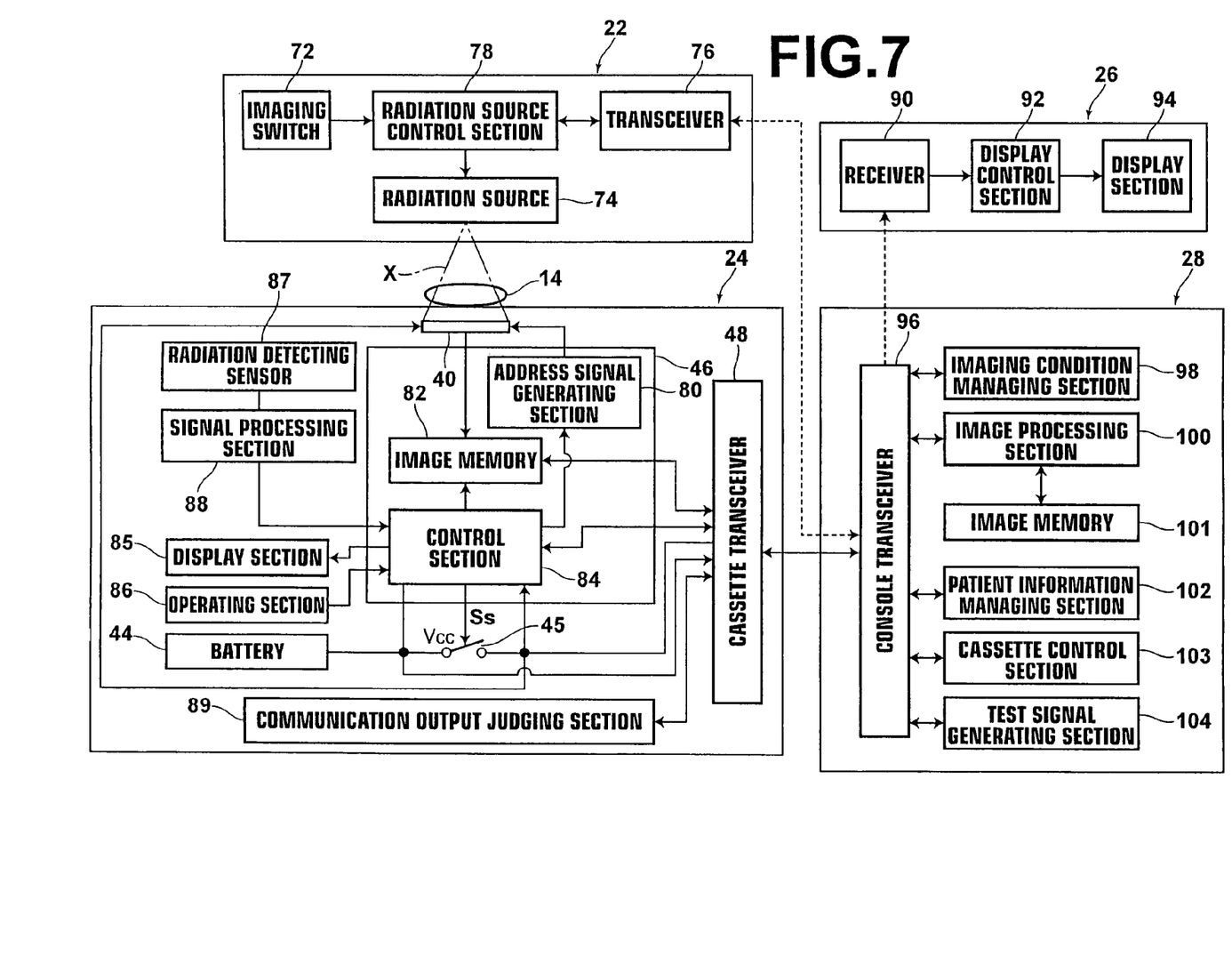
FIG. 7 is a block diagram that illustrates the radiation imaging system of the fourth embodiment.

In the radiation imaging system that employs the fourth embodiment, a test signal generating section 104 that generates test signals is provided within the console 28, and a communication output judging section 89 is provided within the radiation detecting cassette 24, as illustrated in FIG. 7.

Figure 8:
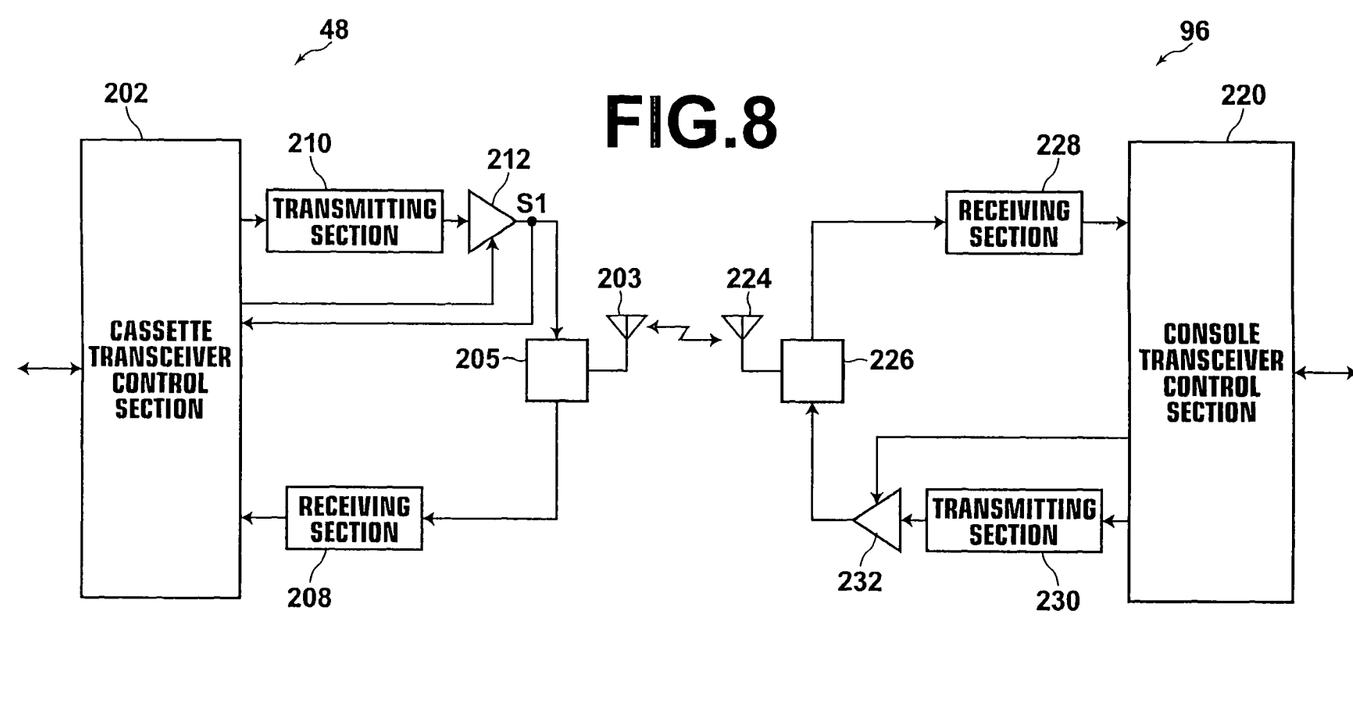
FIG. 8 is a block diagram that illustrates a portion of the inner structures of a cassette transceiver of a radiation detecting cassette and a console transceiver of a console.

In addition, a variable gain amplifier 232 that amplifies signals output from the transmitting section 230 is provided in the console transceiver 96 of the console 28, as illustrated in FIG. 8. The signal strength of wireless signals output from the console transceiver 96 is varied, by varying the gain of the variable gain amplifier 232.

Next, the operation of the radiation imaging system that employs the fourth embodiment will be described.

In the radiation imaging system that employs the fourth embodiment, the signal strength of the console transceiver 96, that is, the gain level of the variable gain amplifier 232, during readout of radiation image signals from the radiation detector 40 is determined after the power switch 45 of the radiation detection cassette 24 is turned ON. The gain level is determined prior to imaging operations of radiation images are initiated.

Specifically, first, a test signal is generated by the test signal generating section 104 of the console 28. The test signal is output to the console transceiver control section 220 of the console transceiver 96. Next, the console transceiver control section 220 outputs the input test signal to the transmitting section 230 at a predetermined transfer rate. The test signal is modulated by the transmitting section 230, amplified by the variable gain amplifier 232, then transmitted to the radiation detecting cassette 24 as a wireless signal via the antenna duplexer 226 and the antenna 224.

At this time, the gain level of the variable gain amplifier 232 is set to a value sufficiently high enough to enable communication between the console 28 and the radiation detecting cassette 24. This gain level is set in advance at the console transceiver control section 220.

The radiation detecting cassette 24 receives the test signal output from the console 28 in the manner described above with the cassette transceiver 48. The received test signal is input to the communication output judging section 89.

The communication output judging section 89 judges whether the signal strength of the input test signal is higher than a minimum signal strength (hereinafter, referred to as "minimum communicable condition") which is capable of being transmitted between the radiation detecting cassette 24 and the console 28. Note that the minimum communicable condition is set in advance by the communication output judging section 89.

In the case that the signal strength of the input test signal is higher than the minimum communicable condition, a signal (hereinafter, referred to as "communication possible signal") indicating this fact is output to the console 28 via the cassette transceiver 48.

The console 28 receives the communication possible signal via the console transceiver 96, and the communication possible signal is input to the console transceiver control section 220. When the communication possible signal is input, the console transceiver control section 220 slightly decreases gain level of the variable gain amplifier 232

Then, the test signal is output again from the test signal generating section 104, output to the transmitting section 230 at the predetermined transfer rate from the console transceiver control section 220, amplified at the lower gain level by the variable gain amplifier 232, and transmitted to the radiation detecting cassette 24 via the antenna duplexer 226 and the antenna 224.

The radiation detecting cassette 24 receives the test signal output from the console 28 with the cassette transceiver 48 as described above. The received test signal is input to the communication output judging section 89.

The communication output judging section 89 judges whether the signal strength of the input test signal is higher than the minimum communicable condition again.

In the case that the signal strength of the input test signal is judged to be higher than the minimum communicable condition, the communication output judging section 89 outputs a communication possible signal to the console 28 via the cassette transceiver 48 again.

The console 28 receives the communication possible signal via the console transceiver 96, and the communication possible signal is input to the console transceiver control section 220. When the communication possible signal is input, the console transceiver control section 220 further decreases the gain level of the variable gain amplifier 232.

Then, the test signal is output again from the test signal generating section 104, output to the transmitting section 230 at the predetermined transfer rate from the console transceiver control section 220, amplified at the lower gain level by the variable gain amplifier 232, and transmitted to the radiation detecting cassette 24 via the antenna duplexer 226 and the antenna 224.

While the radiation detecting 28 keeps on outputting communication possible signals with respect to the test signals output from the console 28 in the manner described above, the console 28 sets the gain level of the variable gain amplifier 232 such that the gain level gradually decreases. Further test signals are amplified at the decreased gain levels, and output to the radiation detecting cassette 24.

In the case that the signal strength of the test signal is judged to be lower than the minimum communicable condition, the communication output judging section 89 outputs a signal (hereinafter, referred to as "communication impossible signal") indicating this fact to the console 28 via the cassette transceiver 48.

The console 28 receives the communication impossible signal via the console transceiver 96, and the communication impossible signal is input to the console transceiver control section 220. When the communication impossible signal is received, the console transceiver control section 220 obtains the gain level which was set immediately previous to the gain level, which is set at that time. This gain level is set as the gain level (hereinafter, referred to as "readout gain level") to be used during readout of radiation image signals from the radiation detector 40. Note that the readout gain level is lower than the gain level which is used at times other than during readout of radiation image signals from the radiation detector 40.

During readout of radiation image signals from the radiation detector 40, the control section 84 of the radiation detecting cassette 24 output a signal indicating that readout is being performed. This signal is output to the console via the cassette transceiver 48.

Various control signals and radiation image signals are output from the console 28 to the radiation detecting cassette 24, the imaging apparatus 22, and the display apparatus 26. While the signal that indicates that readout is being performed is being received by the console transceiver control section 220, the gain level of the variable gain amplifier 232 is set to the readout gain level, which has been obtained in the manner described above. On the other hand, when the signal that indicates that readout is being performed is not being received by the console transceiver control section 220, the gain level of the variable gain amplifier 232 is set to a gain level which is used during standard wireless communications.

In the radiation imaging system that employs the fourth embodiment, during readout of radiation image signals from the radiation detector 40, the signal strength of wireless signals output from the console 28 is set to the minimum strength that enables communication between the console 28 and the radiation detecting cassette 24. Therefore, the influence exerted onto the radiation image signals, which are being read out, by the wireless signals output from the console 28 can be reduced. Accordingly, the amount of noise that occurs in the radiation image signals can also be reduced.

Note that in the radiation imaging system that employs the fourth embodiment, the readout gain was obtained in the manner described above. However, the method by which the readout gain is obtained is not limited to that which was described above. For example, a gain level at which the wireless signals output from the console 28 do not influence the radiation image signals which are being read out may be obtained in advance, and set as the readout gain level. Alternatively, noise levels may be detected from radiation image signals which are being read out, and the gain level may be set to that at which the noise level is lower than a predetermined threshold value.

The radiation detector 40 which is housed in the radiation detecting cassette 24 of the radiation imaging systems of the first through fourth embodiments are those that directly convert the radiation X irradiated thereon to electric signals with the photoelectric converting layer 51. However, the present invention is not limited to using radiation detectors of this type. The radiation detector may be of the indirect conversion type. An example of such a radiation detector is that which converts radiation X irradiated thereon to visible light with a scintillator, then converts the visible light to electric signals using a-Si (amorphous silicon) or the like (refer to Japanese Patent No. 3494683).

In addition, the radiation detector 40 is a TFT readout type radiation detector, that reads out electric charge signals using TFT's. However, the present invention is not limited to using radiation detectors of this type. The radiation detector may be of the optical readout type, that reads out accumulated electric charge signals by having readout light irradiated thereon (refer to U.S. Pat. No. 6,268,614).

What is claimed is:

1. A radiation imaging apparatus, comprising:
   a radiation detecting section that generates electric charges when irradiated with radiation which has passed through a subject, to record a radiation image of the subject;
   a readout section that reads out image signals that represent the radiation image of the subject from the radiation detecting section; and
   a wireless communicating section that reads out the image signals from the readout section and outputs the read out image signals as wireless signals;
   the wireless communicating section decreasing the signal strength of communications during readout of the image signals by the readout section to be lower than the signal strength of communications at times other than during readout of image signals.

2. A radiation imaging system as defined in claim 1, wherein:
   the wireless communicating section sets the signal strength of communications during readout of the image signals to a degree at which the wireless signals output from the wireless communicating section do not influence the image signals which are being read out.

3. A radiation imaging system as defined in claim 1, wherein the second wireless communicating section:
   sets the signal strength of communications during readout of the image signals to a degree at which the wireless signals output from the wireless communicating section do not influence the image signals which are being read out;
   decreases the signal strength of communications in a stepwise manner, to obtain a signal strength at a step which is greater than or equal to a minimum signal strength that enables communications between the radiation imaging apparatus and a receiving apparatus that receives the wireless signals; and sets the obtained signal strength as the signal strength of communications during readout of the image signals; while:

increasing the transfer rate of the wireless signals in a stepwise manner corresponding to the stepwise decrease of the signal strength; and setting the transfer rate of the wireless signals to a speed corresponding to the obtained signal strength.

4. A radiation imaging apparatus, comprising:

a radiation detecting section that generates electric charges when irradiated with radiation which has passed through a subject, to record a radiation image of the subject;

a readout section that reads out image signals that represent the radiation image of the subject from the radiation detecting section; and a wireless communicating section that reads out the image signals from the readout section and outputs the read out image signals as wireless signals;

the wireless communicating section decreasing the transfer rate of the wireless signals during readout of the image signals by the readout section to be lower than transfer rate of the wireless signals at times other than during readout of image signals.

5. A radiation imaging system as defined in claim 4, wherein:

the wireless communicating section sets the transfer rate of the wireless signals during readout of the image signals to a speed at which the wireless signals output from the wireless communicating section do not influence the image signals which are being read out.

\* \* \* \* \*